(12) United States Patent
McCauley et al.

(10) Patent No.: US 10,598,641 B2
(45) Date of Patent: Mar. 24, 2020

(54) METHODS FOR DETERMINING INSTRUMENT LINEARITY AND QUANTIFICATION

(71) Applicant: Thermo Finnigan LLC, San Jose, CA (US)

(72) Inventors: Edward B. McCauley, Cedar Park, TX (US); Scott T. Quarmby, Round Rock, TX (US)

(73) Assignee: THERMO FINNIGAN LLC, San Jose, CA (US)

( * ) Notice: Subject to any disclaimer, the term of this patent is extended or adjusted under 35 U.S.C. 154(b) by 0 days.

(21) Appl. No.: 16/222,089

(22) Filed: Dec. 17, 2018

(65) Prior Publication Data

US 2019/0195843 A1 Jun. 27, 2019

Related U.S. Application Data

(60) Provisional application No. 62/610,890, filed on Dec. 27, 2017.

(51) Int. Cl.
*G01N 30/86* (2006.01)
*H01J 49/00* (2006.01)
*G01N 30/72* (2006.01)

(52) U.S. Cl.
CPC ..... *G01N 30/8679* (2013.01); *G01N 30/7233* (2013.01); *H01J 49/0009* (2013.01); *G01N 30/7206* (2013.01)

(58) Field of Classification Search
USPC ................................................ 250/281, 282
See application file for complete search history.

(56) References Cited

U.S. PATENT DOCUMENTS

2009/0194685 A1* 8/2009 Corr .................... H01J 49/401
250/282

OTHER PUBLICATIONS

Krumwiede et al., "Instrument Performance Standards: A new Concept for fast Routine Performance Checks and Method Development in GC/MS Analysis of Dioxins and Furans", Poster, Dioxin 2010—30th International Symposium on Halogenated Persistent Organic Pollutants (POPs), Sep. 2010.

* cited by examiner

*Primary Examiner* — Kiet T Nguyen
(74) *Attorney, Agent, or Firm* — David A. Schell; Nicholas Cairns

(57) ABSTRACT

A method of assessing the linearity and dynamic range of a mass spectrometer is described comprising analyzing two or more test standards containing positional isomers, for example, using a series of N isomeric analytes with or without an internal standard where N is an integer from 2 to 6 inclusive. The concentrations of the N isomeric analytes may or may not be interleaved between two or more standards. The method allows for repeated instrument characterization without having many of the problems associated with using only a single standard such as octafluoronaphthalene (OFN), for example, persistence, and it may lessen sample carryover issues between adjacent samples. Methods are described using positional isomers of dibromodifluorobenzene in various configurations that show an improved means for qualitative and quantitative analysis of one or more analytes by GC-MS.

19 Claims, 9 Drawing Sheets

1     2     3

4     5     6

7     8     9

METHODS FOR DETERMINING INSTRUMENT LINEARITY AND QUANTIFICATION

FIELD OF THE INVENTION

The present invention relates generally to methods of mass spectrometry and more particularly, it relates to methods of determining linearity and extending quantitative range in mass spectrometry.

BACKGROUND OF THE INVENTION

Demonstration of instrument dynamic range in mass spectrometry generally involves the injection and instrument response observation of a single analyte over several orders of magnitude in concentration. As an example, demonstration of six orders of magnitude in dynamic range may involve performing seven analytical GC runs in order to evaluate the instrument response using an analyte spanning six orders of magnitude in concentration. Following the sequence, it may be a serious challenge to re-characterize the system in a timely manner since the high order standards are persistent in the system and may be difficult to remove completely in a timely manner. A lengthy process is required which may involve cooling of the inlet, ion source and transfer line, followed by replacement of an inlet liner, septa, o-rings and a bakeout of an autosampler syringe. A waste vial may also need to be solvent stripped and baked out prior to re-use in order to prevent analyte run to run carryover. In addition, proper dilution across several orders of concentration is a tedious process and prone to error without using and executing a proper technique. Purchasing certified standards at each level of the test may add considerable cost to the process.

Installation validation for GC-MS often includes analytical testing which may include diagnostic requirements for instrument detection limit (IDL), dynamic range, mass range, mass accuracy, mass stability or any number of requirements set forth by an end user. Demonstration of instrument sensitivity for GC-MS or GC-MS/MS instruments is often performed upon installation utilizing octafluoronaphthalene (OFN) as an analytical test standard. OFN is somewhat unique in offering a high instrument response for a given mass of analyte. This is due in part to the monoisotopic nature of fluorine, the stable polynuclear aromatic structure of the molecular backbone and the high degree of volatility for its molecular weight. This allows OFN to elute early in a chromatographic GC run when other compounds of similar molecular weight still reside on an analytical GC column. Using OFN allows sensitivity criteria based on the molecular ion, mass to charge ratio (m/z or m/e) at 272 Daltons (da) to be used which is largely devoid of background chemical noise.

Determining instrument response characteristics of an analytical tool used for quantitative purposes is fundamental for proper use of the analytical tool. Methods for target compound quantitation often employ a calibration routine in which target analytes of known concentration are analyzed across a predetermined working range of the instrument. Typically, multiple compounds of interest also known as target compounds or analytes are composited in solution at a known concentration. A fraction of this solution, also known as a primary standard, can then be diluted to yield several other solutions with known dilutions. For example, a fraction of a primary solution containing 100 ng/ul of 100 analytes can be diluted two fold, to yield a second standard containing 50 ng/ul of the same 100 analytes. This second standard can subsequently be diluted in the same fashion in order to yield a third 25 ng/uL standard. This process can be repeated as desired in order to yield a set of standards which subsequently, can be individually analyzed. A response curve may be generated for each analyte which correlates instrument response with analyte concentration. An unknown sample may be analyzed, and a quantitative assessment of each analyte of interest in the unknown sample made. The quantitation may be based on a calculated response factor RF, an average response factor $\overline{RF}$, a relative response factor RRF (relative to a fixed concentration internal standard), or average relative response factor $\overline{RRF}$. Additionally, quantitation may be based on an interpolation between neighboring calibration points or an extrapolation from two or more data points. Instrument response may be based on a total ion current (TIC) an extracted ion current profile (EICP), a product ion intensity or peak area of a selected reaction monitoring (SRM) transition, a GC detector such as a flame ionization detector (FID), electron capture detector (ECD) or other chromatographic peak detector. Such methods are well known in the art.

Although non-linear quantitation techniques can in some cases be used, most often it is desired to limit quantitation within a known linear working range of the instrument in order to minimize quantitation errors. This linear range may be defined in terms of a linear fit such as an $R^2$ value or as a maximum deviation such as a % RSD (relative standard deviation) value of the response factors. For many problematic compounds, the response falls off rapidly at lower levels. This may be due to irreversible adsorption, active sites in the chromatographic flow path, etc. Often times the response may roll off at the high end of the calibration curve. This may be due to using too high of an electron multiplier gain for example in mass spectrometer applications. Since response factors can vary significantly between analytes of interest, often times it is desirable to define one working range for one analyte versus another working range for a differing analyte. Since many standards are typically involved in a calibration routine, much time is spent simply calibrating the instrument before any samples can be run. Additionally, serial dilutions of analytical standards can be prone to cumulative error unless a proper technique is employed.

Often times the range over which an instrument is calibrated is set by a methodology employed, and demonstration of linearity within this range may need to be re-generated as part of a laboratory standard operating procedure (SOP) or as part of a regulated method. In general, a calibrated range defines a "working range" of the instrument and calibrations outside of this range are not undertaken. This is due in part to a lengthy process which would be involved in running so many calibration points, but it is also because it is very difficult to run a blank following high-concentration calibration runs. When high levels of analytes are run at upper limits of detection, achieving an acceptable blank run will nearly always require changing chromatograph components such as septa and injection port liners (in the case of GC), flushing autosampler solvent waste vials and syringes and often necessitates baking of such components at high temperature.

It is often desirable to assess a fundamental linearity of a detection system outside of problems encountered by poor chromatography such as irreversible adsorption, decomposition of analytes, etc. This may be referred to as a linear dynamic range of a detector, for example, in a mass spectrometer detection system. It may occur for example as part of an instrument qualification procedure (IQ) wherein the inherent linear dynamic range of a new instrument may be validated. In such a case, a non-problematic analyte may be analyzed near the lower detection limit, and again at increasing concentrations towards an upper limit where detector non-linearity or saturation occurs. As instrument sensitivity and linear dynamic range have improved, a significant problem has arisen. Modern instruments may have a linear dynamic range of around six orders of magnitude or more. Assessment of the full linear dynamic range in such a system if done in a conventional manner may not only be time consuming from the perspective of needing to run many standards, it also should be done successfully the first time otherwise the aforementioned exercises of, for example, changing parts, flushing, baking and blanking, etc., may have to ensue.

Methods have been devised for analyte quantitation which do not involve running a multitude of calibration standards. Instead, positional isomers of a compound are composited together in a single standard which contains differing isomeric forms at concentrations which bracket a targeted working range. Being isomers, the physical properties as well as the mass spectra are very similar. In like manner, so are the instrument response factors. One such method entitled "Instrument Performance Standards: A new Concept for fast Routine Performance Checks and Method Development in GC/MS Analysis of Dioxins and Furans" (online at: https://tools.thermofisher.com/content/sfs/posters/PSDFS1-DirkK-InstrumentPerformanceStandards.pdf) describes such methodology. In this method, a set of six differing tetrachlorodibenzodioxins (TCDD isomers) are composited in a single standard at 2, 5, 10, 25, 50 and 100 fg/uL. This constitutes a standard covering a calibration range of 50 fold. This standard may be used to validate linearity over this working range using a single injection. In general, the actual linear range of an instrument is far in excess of 50 fold and can approach one million fold or more. The above methodology while suitable for demonstrating sensitivity and linearity over a limited concentration range, suffers in applicability over wider ranges due to co-elution effects of various additional isomers, isomeric purity, and analyte carryover.

SUMMARY OF THE INVENTION

Against the above background, the inventive concept described herein solves current problems with broad-based linearity diagnostics in GC-MS, as well as quantitative range when assessing concentrations of unknowns. Embodiments of the present invention may solve carryover problems where analytes of previous runs may interfere significantly with subsequent runs. The method is relatively quick and therefore improves analysis time issues. Dilution errors and cost are other factors that are addressed. Furthermore, the method is suitable for determination of linearity for all modes of operation including full scan, single ion monitoring (SIM), and selected reaction monitoring (SRM) methodologies.

In accordance with an aspect of at least one embodiment there is provided a method of determining mass spectrometer linearity is described, comprising:
(a) Providing N isomeric analytes, wherein N is an integer from 2 to 6 inclusive.
(b) Running the N isomeric analytes in two or three analysis runs. For example, in a two run analysis, a desired instrument response to a N isomeric analyte concentration range may be represented by using a first analysis run comprising a first series of concentrations of the N isomeric analytes and a second analysis run comprising a second series of concentrations of the N isomeric analytes. The two (or three) runs may or may not be interleaved with each other in terms of their concentrations of the N isomeric analytes.
(c) Determining an instrument linearity indicator value from a plot of mass spectrometry response versus concentrations of the N isomeric analytes, wherein the instrument linearity indicator value denotes a critical operating linearity characteristic of a mass spectrometer.

The N isomeric analytes may be selected from positional isomers from formula (I):

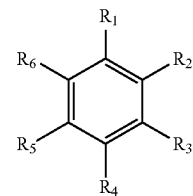

wherein $R_1$, $R_2$, $R_3$, $R_4$, $R_5$ and $R_6$ are independently, H, $C_1$-$C_6$ straight or branched alkyl, alkenyl, alkynyl, F, Cl, Br, $OR_7$, or $SR_7$, wherein $R_7$ is a straight or branched $C_1$ to $C_3$ alkyl. A series of N isomeric analytes may be used comprising positional isomers of dibromodifluorobenzene and may be used in a concentration range in the analysis runs of about 2 to 8 orders of magnitude. Octafluoronaphthalene (OFN) may be present in at least one of the analysis runs and an internal standard may be used to correct for injection-to-injection error. Alternatively or in addition, the mixture of N isomeric analytes may be spiked into unknown samples in order to act as internal standards for quantitation. Quantitative accuracy may be improved by using internal standards of like-intensity to target compound peaks. Quantitation errors may be further reduced by using the internal standards to validate non-detector saturation of high level quantitation's, or act as in-run validation of previous linearity data.

The method may include a third GC-MS run comprising three analysis runs of the N isomeric analytes. The third analysis run of isomeric analytes may or may not be interleaved in concentration with the first and second analysis runs of isomeric analytes. The method may include an analysis using full scan mass spectrometry, using single ion monitoring (SIM) mass spectrometry or selected reaction monitoring (SRM) mass spectrometry.

Instrument linearity may be determined by selecting from an $R^2$ value, a correlation coefficient, a least squares fit, a percent RSD of response factors or a percent RSD of relative response factors. A kit for performing the method is also described.

BRIEF DESCRIPTIONS OF THE DRAWINGS

DETAILED DESCRIPTION

Definitions

Figure 1:
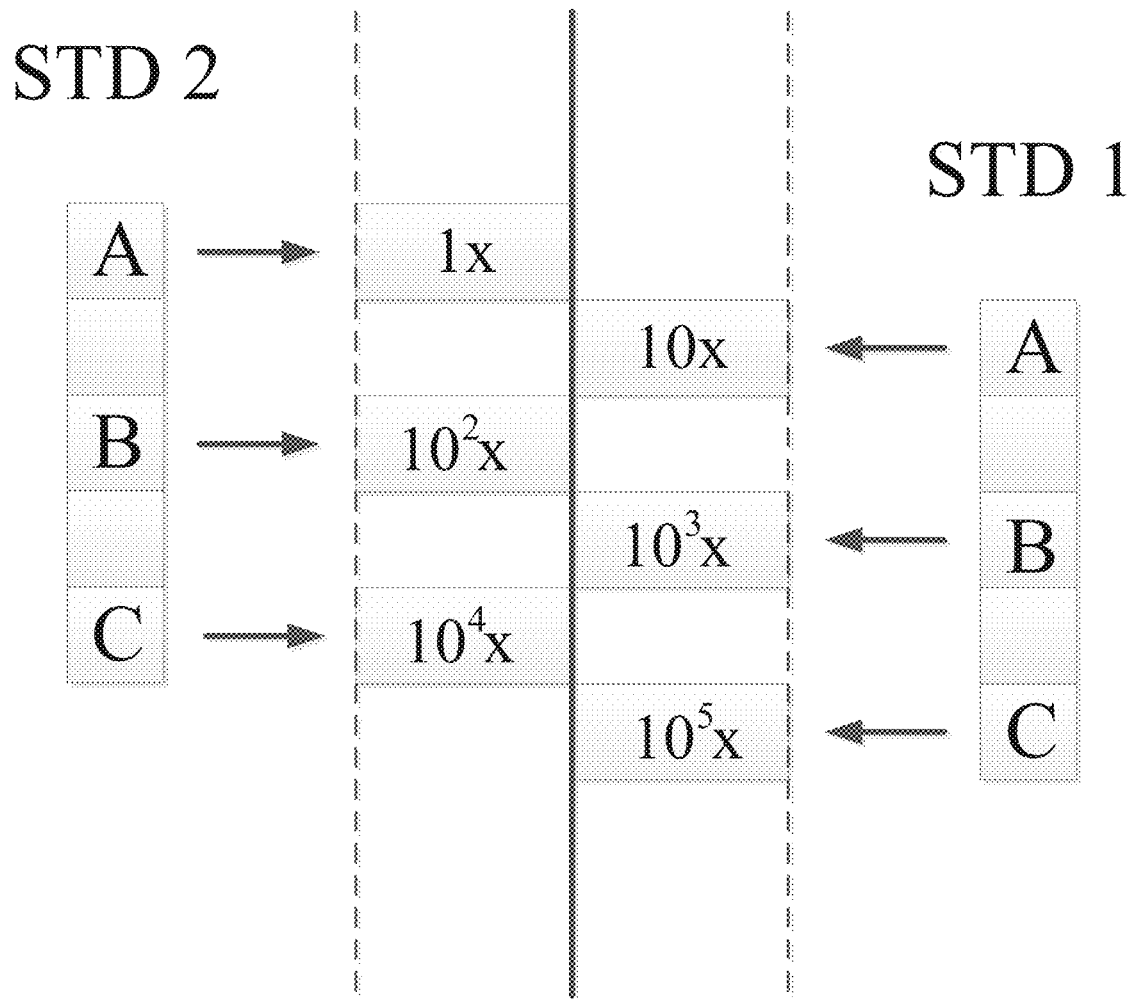
FIG. 1 shows 3 isomers, A, B and C interleaved in decade steps starting at 1× and finishing at $10^5$×. There are two 2 standards, STD1 and STD2.

The term "ppm" as used herein refers to a weight to volume relationship (w/v). 1 ppm thus refers to a solution with a concentration of 1 ng/uL. The term "about" means something that is within plus or minus 5% of a stated value. The term isomer as used herein unless otherwise specified means "positional" isomer, that is, an isomer that is composed of the same number and type of elements (same molecular formula) but where the connectivity of the atoms in the molecule vary between different isomers. For example, ortho and para xylenes are positional isomers each having the molecular formula, $C_8H_{10}$. The term "linearity" is a measure of how closely a particular mass spectrometer responds to a number of analytical standards in varying concentrations of analyte that should give a straight-line instrument response in intensity or peak area. The term "order of magnitude" more refers to something that is ten times more than something else. For example, an analyte, W, with a concentration of 100 ppm is one order of magnitude more than an analyte X with a concentration of 10 ppm; two orders of magnitude more than an analyte Y with a concentration of 1.0 ppm, and one order of magnitude less than an analyte Z with a concentration of 1,000 ppm. The term m/z means mass to charge ratio and is given in Daltons (da). An "instrument response" means that a mass spectrometer system (for example, a GC-MS system, the instrument) provides processed output signals in the form of peaks in a total ion chromatogram (TIC), extracted ion chromatogram (XIC or EIC), SIM, SRM (plots of the responses) that may be shown as plots of intensity or relative abundance against time where peaks may be measured and compared or quantitated in terms of their relative heights or relative areas. Mass spectra (for example, plots of intensity versus m/z ratio and showing molecular ion or fragment peaks) may be extracted from the above and may be used for analyte identification and comparison purposes.

There is a need for a method of mass spectrometry linearity assessment which does not suffer cumulative effects of a series of single standard injections of a persistent analytical standard such as the method described above for OFN. One approach might be to increase the difference in concentration of the isomers employed. Using the isomers at 1, 10, 100, 1,000, 10,000 and 100,000 fg/uL would result in a calibration range of 5 orders of magnitude. Extending the calibration range by using more isomeric forms or by increasing the difference in their concentrations may sound straightforward but may be very problematic in practice. This arises from two sources. First, since a standard may be comprised of isomeric forms of the same chemical structure (for example, by using positional isomers) physical property differences may be very subtle. This may limit the selectable number of employed isomers due to problems arising with co-elution (overlapping peaks). Accurate characterizations of response, particularly when large jumps in concentration between calibration steps are to be done, require complete baseline separation of isomers.

The second problem which arises when attempting to extend a calibration range with this methodology is also related to a potential set of positional isomers. Invariably, analytical standards are not completely pure. Chemicals which have isomeric variants in particular, may often be contaminated with trace levels of other isomeric forms. This can arise from synthetic pathways which result in small levels of alternative isomeric forms, or can arise from difficulty in separating very similar compounds. Impurities as high as a few percent may be tolerated for calibration ranges of only two orders of magnitude or so, but are unacceptable when larger ranges are to be covered.

In an embodiment of the present invention, a first standard is composited comprising isomeric forms of a molecule, for example, A, B and C, all positional isomers. As an example, the difference in concentration of the isomeric forms in the standard is selected to be 100 fold. If X represents a concentration such as fg/uL, ppm, etc., a first standard may have a distribution in concentrations as follows, where the concentration of B is 100 times that of A and where the concentration of C is 100 times that of B (for example, as in Table 1):

TABLE 1

| Isomeric form | Concentration |
| --- | --- |
| A | 10X |
| B | 1,000X |
| C | 100,000X |

A simple 10 fold dilution of this first standard will result in a second standard with the following concentrations (Table 2):

TABLE 2

| Isomeric form | Concentration |
| --- | --- |
| A | 1X |
| B | 100X |
| C | 10,000X |

When these two standards are evaluated independently, peaks areas varying by five orders of magnitude are represented within two analytical runs. This method of staggering concentrations between standards is herein referred to as "isomer interleaving" or just, "interleaving" and can be represented as shown in FIG. 1.

A significant advantage of compositing standards in this fashion is that each isomer only differs by a factor of 10 in concentration between the standards. This may render carryover issues from injection-to-injection negligible, as typical carryover is less than 0.1%. If for example a dynamic range representation is carried out by a given number of isomers over a given concentration range, and it is found that the detector gain is set too high, the gain can be reduced and the linearity check repeated without the aforementioned problems with carryover, requiring a time consuming need for changing components, baking them out, running instrument blanks, etc.

A second advantage of compositing standards in this fashion is that the number of isomeric forms needed to evaluate the dynamic range may be half that which would be required otherwise. For example, six data points can be used to demonstrate five orders of linearity. A set of isomers such as A, B, C, D, E and F may be composited as a single test standard for this assessment or representation as performed conventionally. If there are interference issues with co-elution concerning some of the isomers such as D, E and F, it may be necessary to composite these in a second standard such that one standard contains A, B and C, while the other standard contains D, E and F. While this resolves the co-elution issue, it requires six standards instead of three. This compounds the risk of trace impurities being present and can add considerable cost to the process. Only a few commercially available isomers may be available for purchase, or some of the isomers may have problems related to cost, toxicity, or long term stability. Optionally, adding another isomer D to the mixture represented in FIG. 1. would result in seven orders of magnitude in dynamic range representation.

Figure 2:
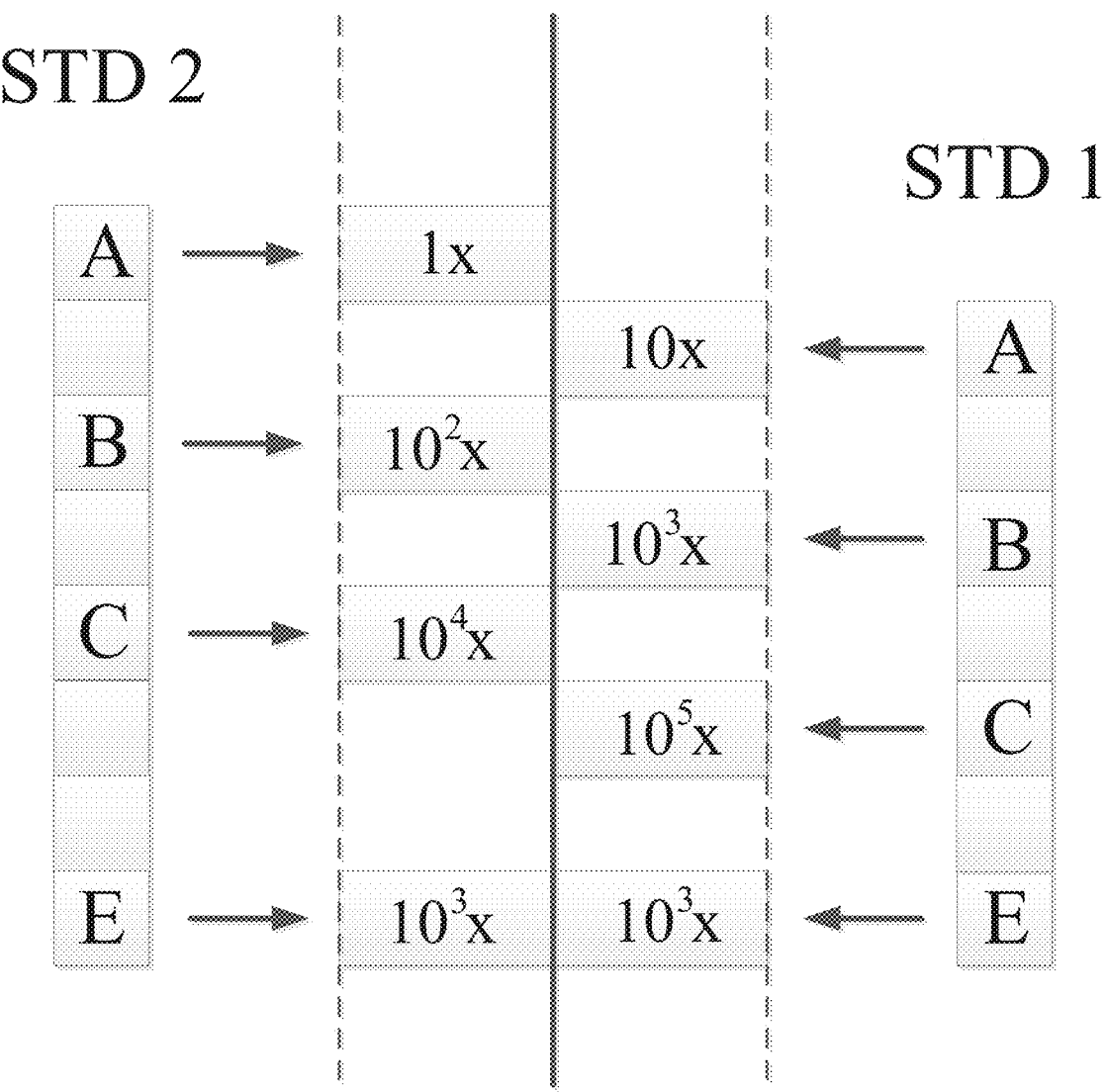
FIG. 2 shows an embodiment containing a non-interleaved standard containing four isomers, A, B, C and E.

Errors associated with injection-to-injection reproducibility are well-known. These may occur when the amount of sample injected is not exactly the same from one injection to the next. This could occur, for example, if slightly different amounts of liquid were drawn into a volume measuring syringe in different runs. Compensation for this error is often done by adding an internal standard for each analysis, wherein the internal standard is constant in concentration for each analysis. A correction factor may then be applied which corrects for injection-to-injection error. This may be performed by normalizing the instrument response as shown in the commonly used relative response factor equation. An ideal internal standard for this correction may be yet another isomer of the analytes used or it could be an unrelated compound. An isomer E may be added to each of the two standards represented in FIG. 1 which is present at the same concentration. The concentration of this standard ideally resides at some mid-level concentration such that there is good signal intensity without approaching saturation. This is represented in FIG. 2. The internal standard selected for correction may or may not be a positional isomer of the other isomers used. It may or may not be added to standards at the user's discretion.

Figure 3:
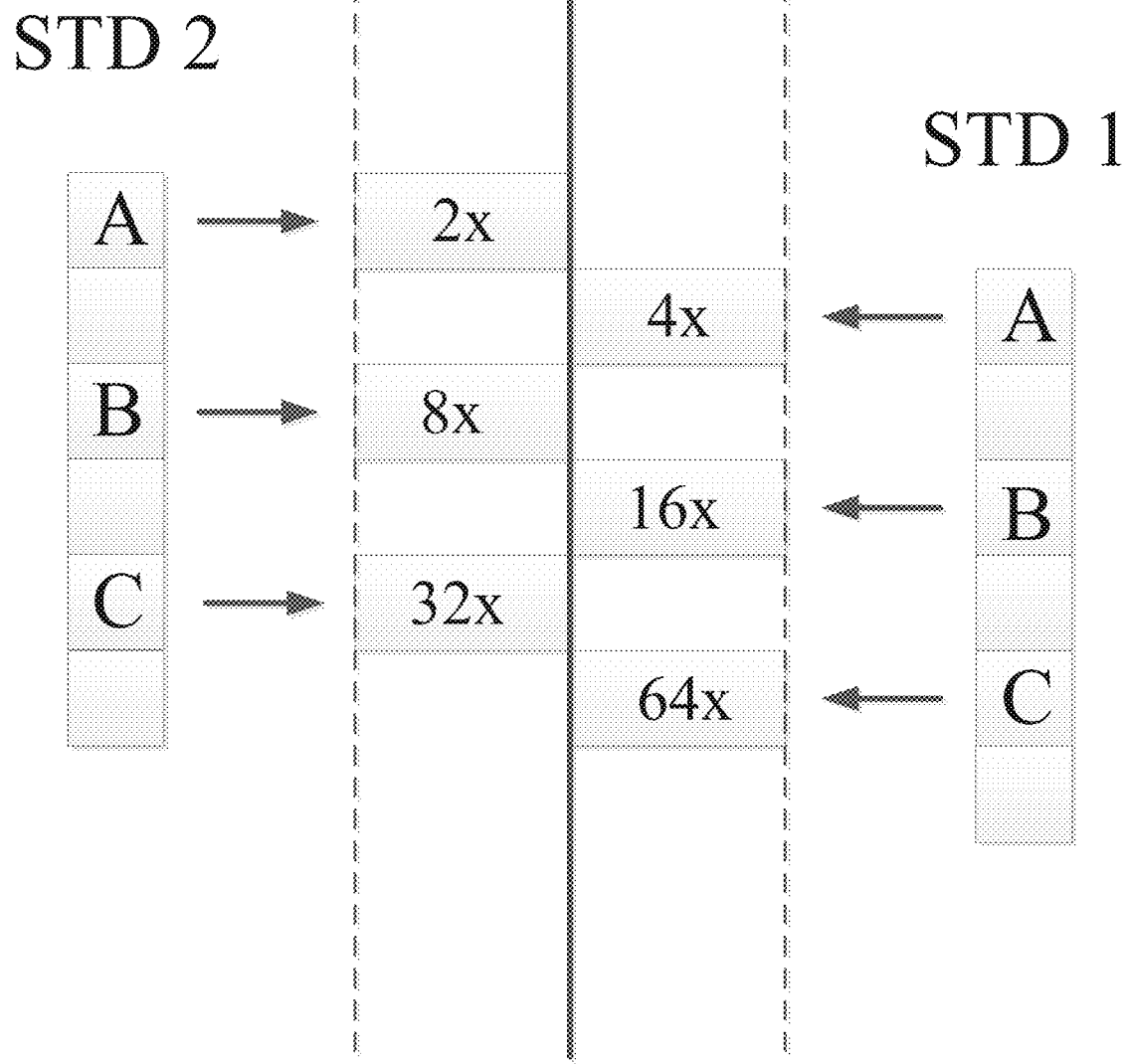
FIG. 3 shows 3 isomers interleaved in binary steps between 2 standards.

The preceding examples illustrating positional isomer interleaving are not restricted to 10 times increases in concentration, or even whole number values in concentration. If for example a quantitation method requires a limited range of quantitation wherein a more accurate quantitation may be accomplished, or if some of the isomers in question are extremely costly, it may be desirable to interleave over a shorter range in concentration. The examples given above are not meant to limit the scope of the present inventive concept and one skilled in the art would recognize that many other steps in concentration ranges according to the same principle and whether interleaved or not, may be used. A further example of which is shown in FIG. 3 (example of binary interleaving, standard #1 can be diluted two fold to yield standard #2). This binary range is given as an example of a binary range and may be extended as the user desires.

Figure 4:
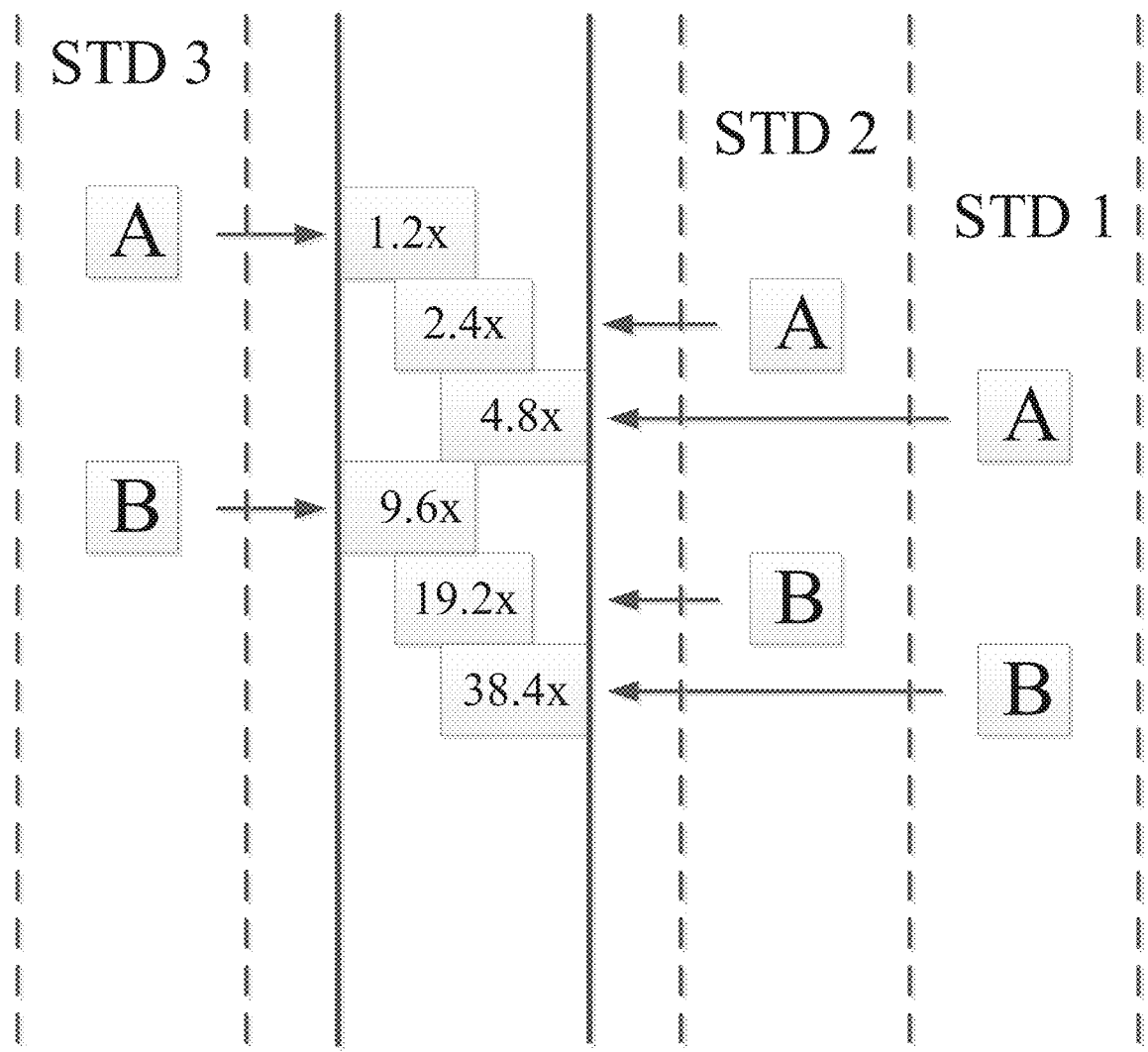
FIG. 4 shows an example of higher order interleaving using three standards and a 1.2× base that ends at 38.4×.

Embodiments according to FIGS. 1 and 3 constitute the simplest form or "first order" standard interleaving. A "second order" interleaving technique may be employed wherein, for example, a third standard is employed or where analyte concentrations are not "order of magnitude" or binary" spaced but are spaced at other, less common intervals over a given range. This is shown diagrammatically in FIG. 4. This technique may be used when isomeric forms are very limited, expensive, toxic, more contaminated or when a differing isomer constitutes the target analyte for quantitation. A common internal standard for response normalization may be added as shown in FIG. 2.

Instrument Detection Limit.

In general, the linear dynamic range of an analytical instrument is only one figure of merit in an instrument qualification assessment. Of equal importance is the minimum detectable quantity of a substance. Since the minimum detectable quantity of a substance depends on the substance and instrument in question, certain industry standards have been adopted. In the case of GC-MS and GC-MS/MS analysis, this industry standard is octafluoronaphthalene (OFN).

OFN has some unique properties which make it very easy to detect at low levels in mass spectrometry. First, it has a high volatility relative to its molecular mass. This allows it to elute from a chromatograph early in an analytical run before compounds of similar mass (isobaric interferents) have a chance to do so, thereby largely avoiding interferences caused by common masses. Such common masses may occur by virtue of a residual hydrocarbon presence. Hydrocarbons are ubiquitous in nature, being produced both naturally and through artificial means. Hydrocarbon fluids are also commonly used in mass spectrometer foreline mechanical vacuum pumps and can contribute to the instrument background if not carefully managed.

A second advantage of using OFN relates to the monoisotopic nature of the fluorine atom which results in an enhanced molecular ion. The molecular ion of OFN is also its base peak (the most intense ion in the spectrum). The methods described herein are applicable at least to chemical ionization and to electron impact ionization GC-MS.

Figure 5:
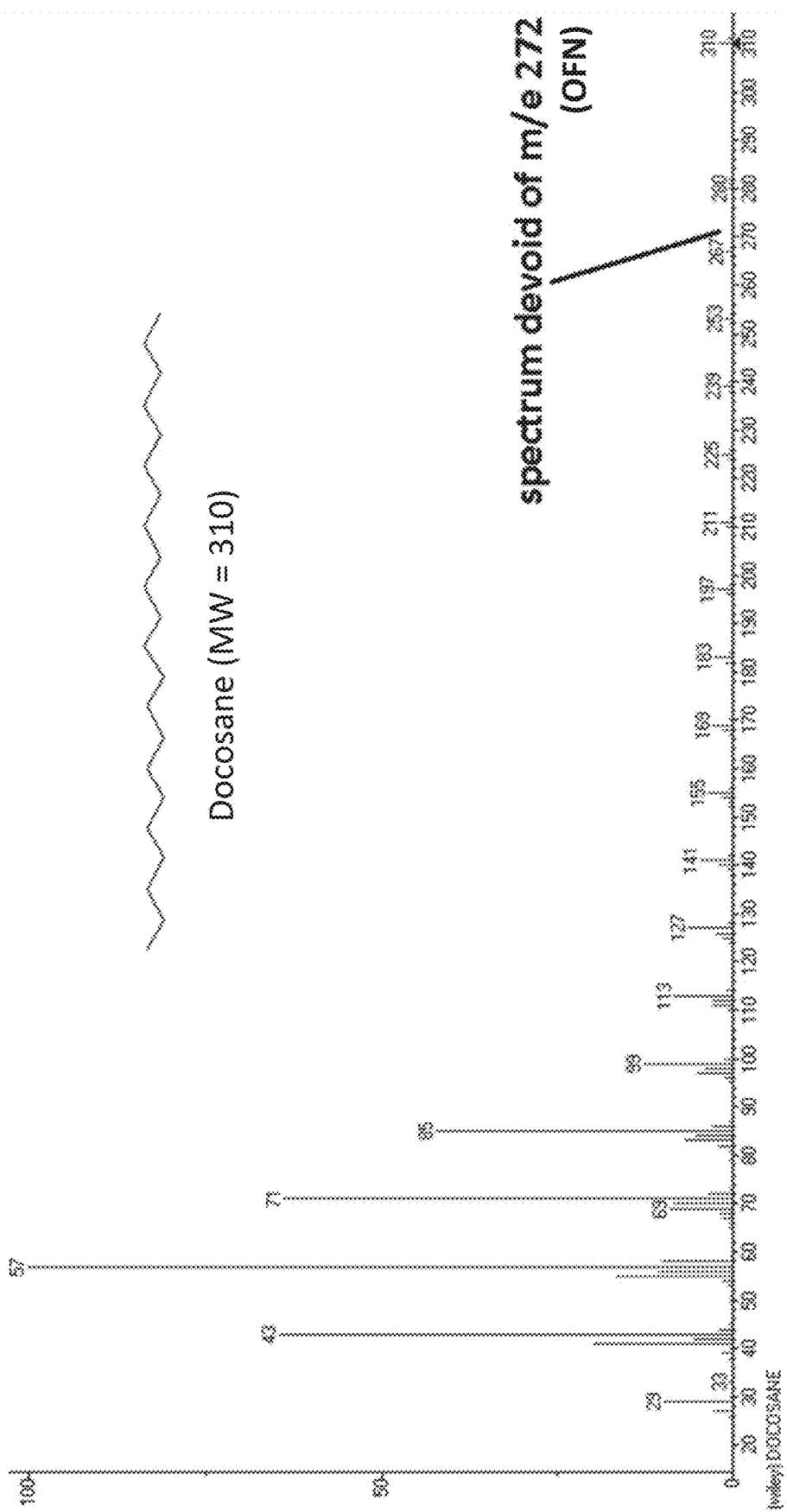
FIG. 5 shows a mass spectrum of docosane.

A third advantage of using OFN is that it has a resonance stabilized cyclic structure which also contributes to its stability and affords a strong molecular ion intensity. A fourth advantage of using OFN is that it occurs in a m/z "valley" where common background ions are relatively low. Common hydrocarbon background ions are fewer in this mass range since hydrocarbons largely fragment in 14 Dalton units due to methylene group (—$CH_2$—) cleavage. This is illustrated for the primary or n-alkane Docosane ($C_{22}H_{46}$) in FIG. 5 (spectrum of docosane showing valleys between ion clusters due to methylene group cleavage. Adding methylene groups to give higher weight n-alkanes such as Tricosane ($C_{23}H_{48}$) or Tetracosane ($C_{24}H_{50}$) result in similar spectra with a similar valley in the vicinity of m/z 272 da (m/z of OFN). The ordinate is relative abundance (0 to 100%) or intensity and the abscissa is m/z.

From the above discussion OFN could be analyzed at ever increasing concentrations using multiple standards in order to establish the working range of the instrument. However, since OFN has no other positional naphthalene-based isomers, using octafluoronaphthalene isomeric standard interleaving is not possible with this compound alone.

A class of compounds is identified herein which share many of the desirable attributes of OFN and make them suitable for use as mass spectrometry standards. This class of compounds comprises isomers of dibromodifluorobenzene (DBDFB). Isomers of DBDFB exhibit a base mass (most abundant ion) of m/z 272 da in like manner to OFN. They are relatively volatile for their mass and incorporate a cyclic structure which lends toward high stability and low fragmentation losses. Isomers of DBDFB are readily available. They are low cost, chemically stable, and enough forms are available to allow isomer selection that avoids co-elution problems and isomer contamination problems.

Figure 6:
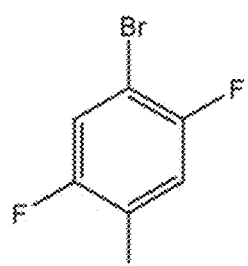
FIG. 6 shows nine isomers of dibromodifluorobenzene (DBDFB).
Figure 6:
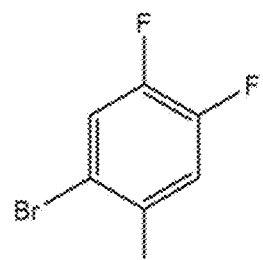
Figure 6:
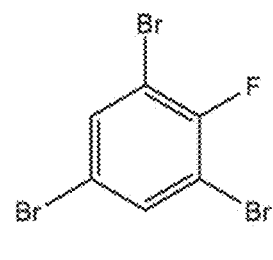
Figure 6:
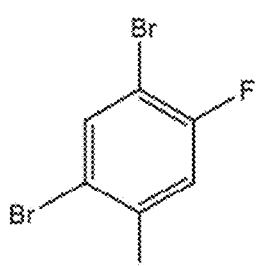
Figure 6:
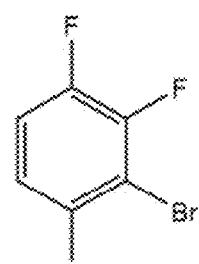
Figure 6:
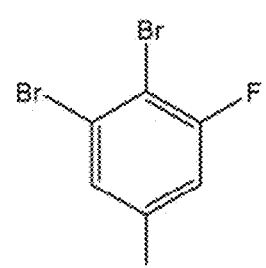
Figure 6:
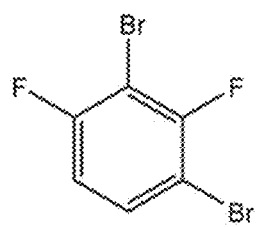
Figure 6:
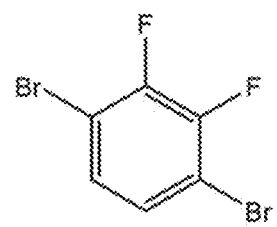
Figure 6:
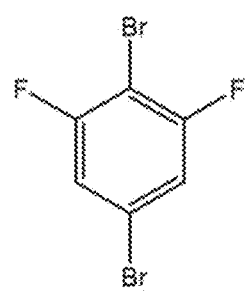

FIG. 6 illustrates some of the DBDFBs (structures 1-9) currently available for purchase from Sigma-Aldrich.

Figure 7:
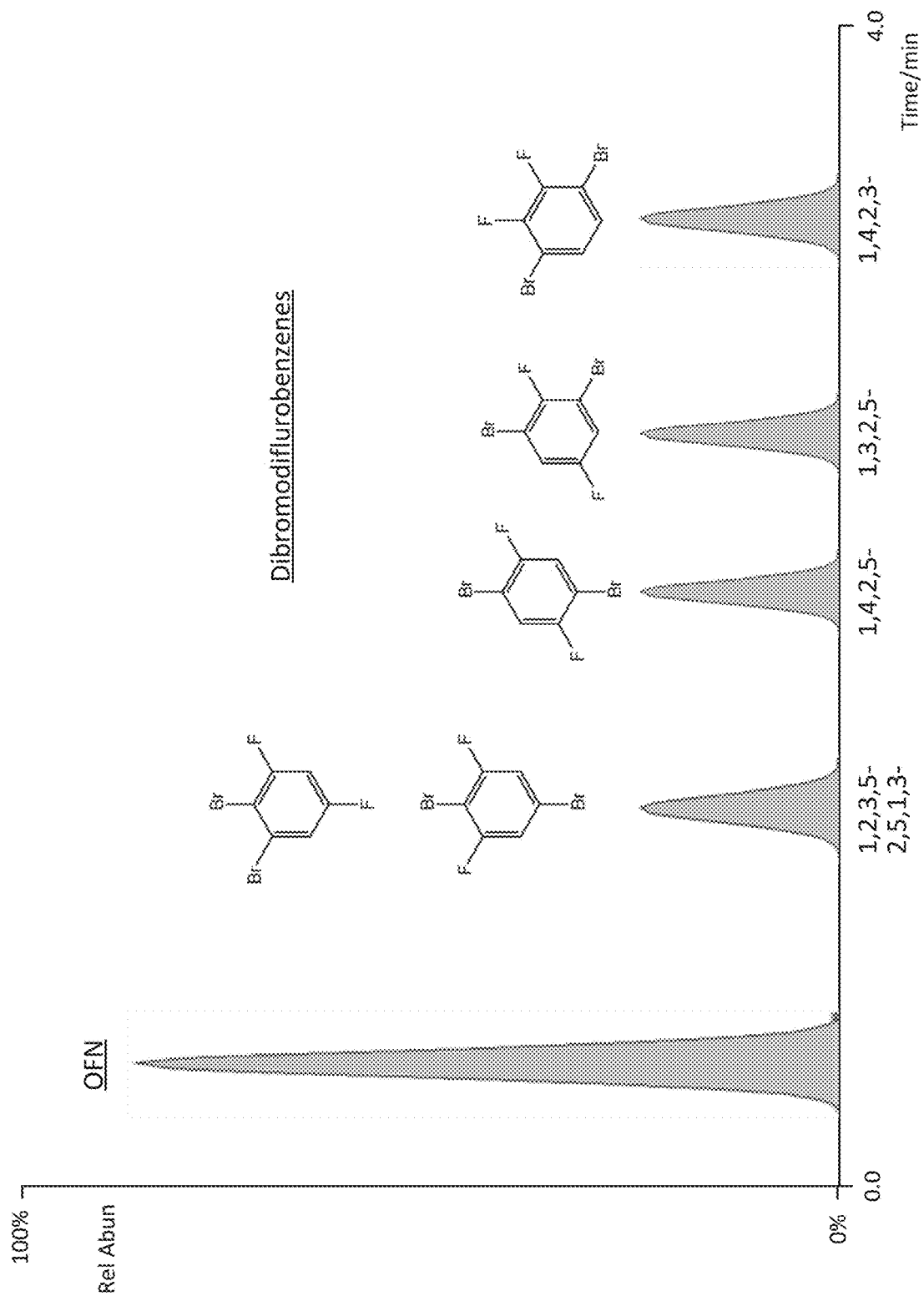
FIG. 7 shows an ion chromatogram of OFN and four isomers of DBDFB

FIG. 7 illustrates a plot of m/z 272 da ion abundance using a split injection of OFN as well as four isomers of DBDFB at equivalent concentrations. It illustrates full separation of four DBDFB isomers including OFN within four minutes. As seen, the responses of the various DBDFB isomers are very similar in intensities. The 2,5,1,3-isomer was not used as it co-elutes with the 1,2,3,5-isomer under the GC-MS conditions used for the analysis. Splitless injections may also be made. As seen in the chromatogram, the OFN response is about twice than that of the DBDFB isomers, while the responses (intensities and peak areas) of the DBDFB isomers are very similar. Using the four isomers shown in FIG. 7, a standard kit may be composited with concentrations, for example, in accordance with FIG. 1. This would allow for linearity assessment across seven orders of magnitude. OFN may additionally be spiked into one of the standards at an appropriate (normalized) concentration in order to establish a point at the low end of the curve. Instructions for use as well as Material Safety Data Sheets and other informational content may be provided with such a kit.

Figure 8:
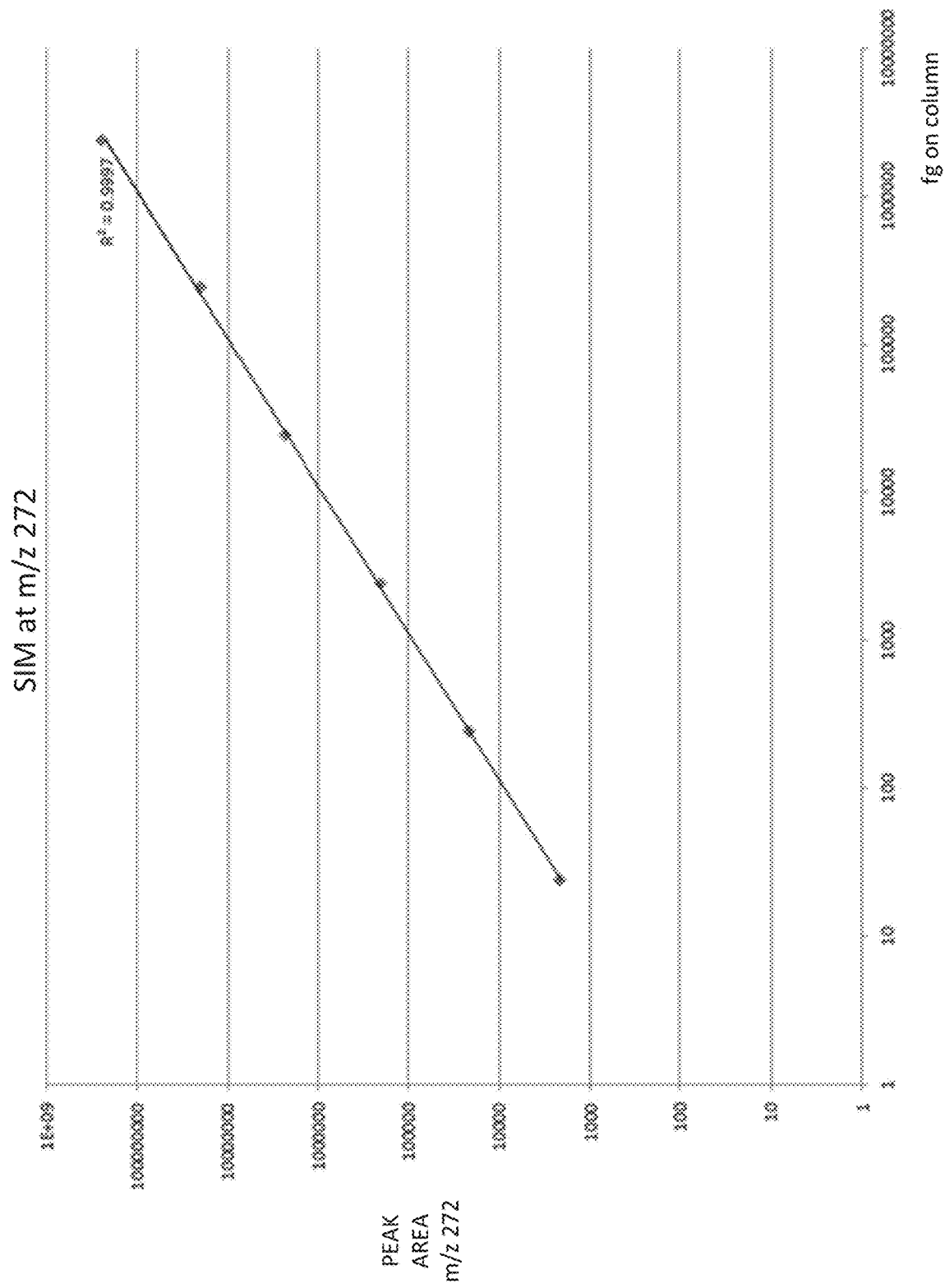
FIG. 8 shows a linearity plot and $R^2$ value for data gathered in SIM mode using DBDFB mixtures in accordance with the embodiment of FIG. 1.

FIG. 8 shows a linearity plot and $R^2$ value of 0.9997 for data gathered in SIM mode using DBDFB mixtures in accordance with the embodiment as shown in FIG. 1.

Figure 9:
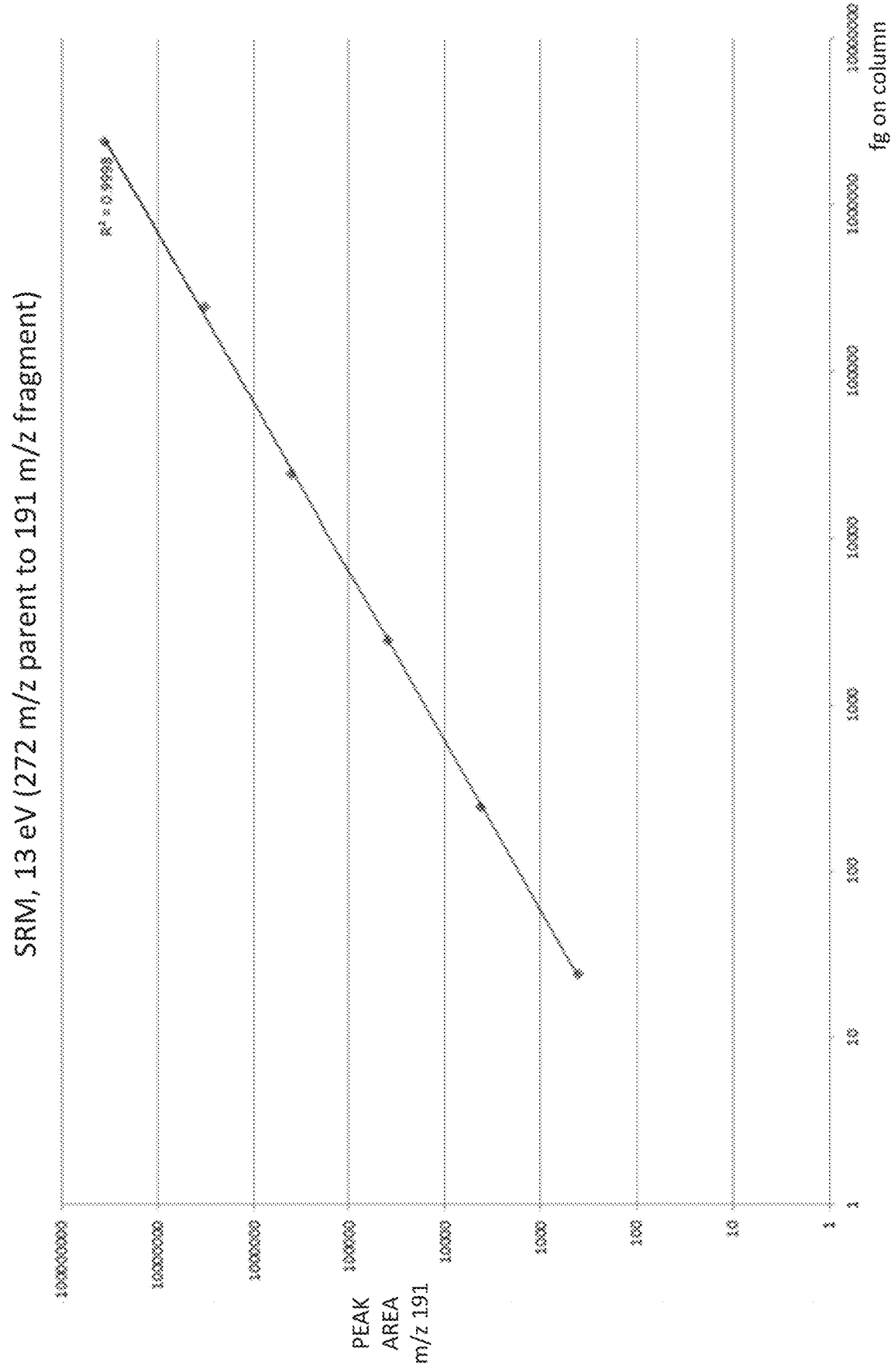
FIG. 9 shows a linearity plot and $R^2$ value for data gathered in SRM mode using DBDFB mixtures in accordance with the embodiment of FIG. 1.

FIG. 9 shows a linearity plot and $R^2$ value of 0.9998 for data gathered in SRM mode using a product ion at m/z 191 da in the DBDFB mixtures in accordance with the embodiment as shown in FIG. 1

Quantitation.

Internal standard or external standard methods of quantitation may be performed using this method by running a series of analytes as in the method above for the N isomeric analytes. For internal standard quantitation, one or more of the series of analytes may serve as an internal standard. Internal standard techniques are well known, and calculate concentrations based on a previously generated relative response factor (RRF) for each analyte of interest in accordance with the following equation:

$$RRF_n = \frac{A_n \times C_{is}}{A_{is} \times C_n}$$

Wherein:
$A_n$ is the detector response of an analyte n.
$A_{is}$ is the detector response of an internal standard.
$C_{is}$ is the concentration of the internal standard.
$C_n$ is the concentration of analyte n.

Subsequent to evaluation of the RRF's for a known concentration range of isomeric forms, an unknown concentration of a differing isomer may be determined by solving the above equation for $C_n$, and applying a relative response factor or average relative response factor calculated from one or more differing isomers. The quantitation of the unknown will be accurate, since the response factor of isomers generally fall within a narrow margin. In like manner, external standard quantitation may be employed based on an absolute response factor determined in accordance with the following equation:

$$RF_n = \frac{A_n}{C_n}$$

These methods may be used independently to determine an unknown concentration of an isomer, or by using a combination of the above two methods, or by using the corresponding $\overline{RRF}$ or $\overline{RF}$ values.

Instrument linearity may be determined by selecting from an $R^2$ value, a correlation coefficient, a least squares fit, a percent RSD of response factors or a percent RSD of relative response factors.

The specific embodiments described herein incorporate details to facilitate the understanding of principles of construction and operation of the invention. Such reference herein to specific embodiments and details thereof is not intended to limit the scope of the claims appended hereto. It will be readily apparent to one skilled in the art that various other modifications may be made in the embodiments chosen for illustration without departing from the spirit and scope of the invention as defined by the claims. For example, there are very large number of molecular positional isomers or other isomers that one skilled in the art would recognize that may be substituted for the set of DBDFB isomers as used herein.

What is claimed is:

1. A method of determining mass spectrometer linearity, comprising:
    (a) providing N isomeric analytes, wherein N is an integer from 2 to 6 inclusive;
    (b) running the N isomeric analytes in two analysis runs; wherein a first analysis run is performed using a first series of concentrations of the N isomeric analytes and a second analysis run is performed using a second series of concentrations of the N isomeric analytes interleaved in concentration with the first series of concentrations of the N isomeric analytes; and,
    (c) determining an instrument linearity indicator value from a plot of mass spectrometry response versus concentrations of the N isomeric analytes, wherein the instrument linearity indicator value denotes a critical operating linearity characteristic of a mass spectrometer.

2. The method of claim 1, wherein the N isomeric analytes are selected from positional isomers from formula (I):

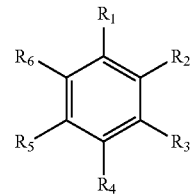

wherein $R_1$, $R_2$, $R_3$, $R_4$, $R_5$ and $R_6$ are independently, H, $C_1$-$C_6$ straight or branched alkyl, alkenyl, alkynyl, F, Cl, Br, $OR_7$, or $SR_7$, wherein $R_7$ is a straight or branched $C_1$ to $C_3$ alkyl.

3. The method of claim 2, wherein the series of N isomeric analytes comprises positional isomers of dibromodifluorobenzene.

4. The method of claim 1, wherein N is an integer from 3 to 5.

5. The method of claim 1, wherein N is 4.

6. The method of claim 1, wherein the N isomeric analytes comprise a range in concentration in the analysis runs of about 2 to 8 orders of magnitude.

7. The method of claim 1, wherein octafluoronaphthalene is present in at least one of the analysis runs in place of one of the N isomeric analytes.

8. The method of claim 1, wherein an internal standard is added.

9. The method of claim 1, wherein a third series of concentrations of the N isomeric analytes is added.

10. The method of claim 9, wherein the third analysis run of isomeric analytes is interleaved in concentrations with the first and second analysis runs of isomeric analytes.

11. The method of claim 1, wherein a gas chromatography mass spectrometer (GC-MS) analysis is performed using full scan mass spectrometry.

12. The method of claim 1, wherein a gas chromatography mass spectrometer (GC-MS) analysis is performed using single ion monitoring mass spectrometry.

13. The method of claim 1, wherein a gas chromatography mass spectrometer (GC-MS) analysis is performed using selected reaction monitoring mass spectrometry.

14. The method of claim 1, wherein the mass spectrometer linearity is determined by selecting from the group consisting of, a coefficient of determination ($R^2$) value, a correlation coefficient, a least squares fit, a percent relative standard deviation (RSD) of response factors or a percent RSD of relative response factors.

15. The method of claim 1 wherein a desired concentration range covers 3, 4, 5, 6, 7, or 8 orders of magnitude.

16. The method of claim 1 wherein a desired concentration range comprises a binary concentration range.

17. The method of claim 1 wherein a desired concentration range is a second order concentration range.

18. The method of claim 1 wherein a concentration difference between any two successive concentrations of the N isomeric analytes in either concentration series is at least a factor of 2.

19. A method of mass spectrometry quantitation, comprising:
(a) providing N isomeric analytes, wherein N is an integer from 2 to 6 inclusive;
(b) running the N isomeric analytes in two analysis runs; wherein a first analysis run is performed using a first series of concentrations of the N isomeric analytes and a second analysis run is performed using a second series of concentrations of the N isomeric analytes interleaved in concentration with the first series of concentrations of the N isomeric analytes;
(c) determining an instrument response versus concentrations of the N isomeric analytes; and,
(d) quantifying an isomer based on the response versus concentrations of the N isomeric analytes.

* * * * *